United States Patent
Shakespeare

(10) Patent No.: US 7,545,971 B2
(45) Date of Patent: Jun. 9, 2009

(54) METHOD AND APPARATUS FOR MEASURING THE CREPE OF A MOVING SHEET

(75) Inventor: John F. Shakespeare, Kuoplo (FI)

(73) Assignee: Honeywell International Inc., Morristown, NJ (US)

(*) Notice: Subject to any disclaimer, the term of this patent is extended or adjusted under 35 U.S.C. 154(b) by 676 days.

(21) Appl. No.: 11/209,586

(22) Filed: Aug. 22, 2005

(65) Prior Publication Data
US 2008/0013818 A1 Jan. 17, 2008

(51) Int. Cl.
G06K 9/00 (2006.01)

(52) U.S. Cl. .......................................... 382/141; 702/35

(58) Field of Classification Search ................. 382/141
See application file for complete search history.

(56) References Cited

U.S. PATENT DOCUMENTS

| | | | |
|---|---|---|---|
| 4,100,017 A | | 7/1978 | Flautt |
| 4,372,309 A | | 2/1983 | Flowler |
| 4,519,041 A | | 5/1985 | Fant et al. |
| 4,752,897 A | * | 6/1988 | Zoeller et al. ............... 382/141 |
| 4,818,930 A | | 4/1989 | Flemming et al. |
| 4,931,657 A | | 6/1990 | Houston et al. |
| 5,068,799 A | * | 11/1991 | Jarrett, Jr. .................... 702/40 |
| 5,104,488 A | | 4/1992 | Chase |
| 5,138,878 A | | 8/1992 | Cresson et al. |
| 5,150,175 A | * | 9/1992 | Whitman et al. ............ 356/429 |
| 5,324,475 A | | 6/1994 | Okahashi |
| 5,328,565 A | * | 7/1994 | Rasch et al. ................. 162/111 |
| 5,533,139 A | * | 7/1996 | Parker et al. ................. 382/108 |

(Continued)

FOREIGN PATENT DOCUMENTS

CA 2012351 9/1990

(Continued)

OTHER PUBLICATIONS

J. Scharcanski and C. Dodson, "Stochastic Texture Image Estimators for Local Spatial Anisotropy and Its Variability", Oct. 2000, IEEE, IEEE Transactions on Instrumentation and Measurement, vol. 49, No. 5, pp. 971-978.*

(Continued)

*Primary Examiner*—Matthew C. Bella
*Assistant Examiner*—Sath V. Perungavoor
(74) *Attorney, Agent, or Firm*—Cascio Schmoyer & Zervas

(57) ABSTRACT

An image-based measurement technique that directly measures the crepe pattern on a moving sheet employs a suitable arrangement of illumination, optical elements, and an imaging device to obtain digital images of the sheet surface. The image resolution is sufficient to represent tissue crepe folds at the scale of the crepe. A spectral analysis of some or of all the images reveals the crepe folding pitch. Further analysis of the image optionally reveals other crepe structural parameters, such as the distribution of crepe fold orientation angles and distribution of linear fold lengths. Corrective actions can be implemented in response to changes in the crepe structure. The pitch of creping is the primary parameter for describing the crepe pattern; in addition, analyzing the images with a gradient operator can yield information regarding the orientation of the crepe folds and distribution of angles of the crepe furrows on the hood side or equivalently of the crepe seams on the cylinder side.

37 Claims, 6 Drawing Sheets

U.S. PATENT DOCUMENTS

| | | | |
|---|---|---|---|
| 5,581,637 A | 12/1996 | Cass et al. | |
| 5,640,244 A | 6/1997 | Hellstrom et al. | |
| 5,654,799 A | 8/1997 | Chase | |
| 5,684,530 A * | 11/1997 | White | 348/131 |
| 5,699,163 A | 12/1997 | Todoroki et al. | |
| 5,764,874 A | 6/1998 | White | |
| 5,865,824 A * | 2/1999 | Chen et al. | 604/378 |
| 6,108,436 A * | 8/2000 | Jansen et al. | 382/112 |
| 6,111,651 A | 8/2000 | Shakespeare | |
| 6,259,109 B1 | 7/2001 | Dalmia et al. | |
| 6,272,440 B1 * | 8/2001 | Shakespeare et al. | 250/559.04 |
| 6,441,904 B1 | 8/2002 | Shakespeare | |
| 6,606,394 B1 | 8/2003 | Park et al. | |
| 6,614,918 B1 * | 9/2003 | Fujita | 382/141 |
| 6,643,022 B1 | 11/2003 | Komppa | |
| 6,678,670 B2 * | 1/2004 | Abbisso et al. | 706/44 |
| 6,717,675 B1 | 4/2004 | Munch | |
| 6,750,992 B1 * | 6/2004 | Holub | 358/504 |
| 6,787,213 B1 | 9/2004 | Beuther | |
| 6,799,083 B2 | 9/2004 | Chen et al. | |
| 6,977,757 B1 * | 12/2005 | Takahashi et al. | 358/3.05 |
| 7,120,515 B2 * | 10/2006 | Floeder et al. | 700/122 |
| 2002/0039181 A1 | 4/2002 | Shakespeare et al. | |
| 2002/0052700 A1 | 5/2002 | Shakespeare | 702/35 |
| 2002/0097320 A1 | 7/2002 | Zalis | |
| 2002/0154325 A1 * | 10/2002 | Holub | 358/1.9 |
| 2002/0159618 A1 | 10/2002 | Freeman et al. | |
| 2003/0131959 A1 * | 7/2003 | Marinack et al. | 162/111 |
| 2003/0144747 A1 | 7/2003 | Shakespeare | |
| 2003/0156293 A1 | 8/2003 | Kazuhiko et al. | |
| 2004/0037465 A1 | 2/2004 | Krause | |
| 2004/0175043 A1 | 9/2004 | Lee | |
| 2004/0243270 A1 | 12/2004 | Amirthalingam | |
| 2004/0246510 A1 | 12/2004 | Jacobsen et al. | |
| 2005/0004956 A1 | 1/2005 | Pourdeyhimi | |
| 2005/0075801 A1 | 4/2005 | Skeps et al. | |
| 2006/0207735 A1 * | 9/2006 | Blanz et al. | 162/111 |
| 2006/0237156 A1 * | 10/2006 | Shakespeare et al. | 162/198 |
| 2008/0013818 A1 * | 1/2008 | Shakespeare | 382/141 |

FOREIGN PATENT DOCUMENTS

| | | |
|---|---|---|
| DE | 34 13 558 C2 | 10/1985 |
| DE | 40 08 366 A1 | 9/1990 |
| EP | 0 612 977 A2 | 8/1994 |
| FR | 2620823 | 3/1989 |

OTHER PUBLICATIONS

Scharcanski J. et al., Texture Analysis for Estimating Spatial Variability and Anisotropy in Planar Stochastic Structures, Optical Engineering, US, Aug. 1996, pp. 2302-2309.

Arivazhagan S et al., Texture Segmentation Using Wavelet Transform, Pattern Recognition Letters, Amsterdam NL, vol. 24, No. 16, Dec. 2003, pp. 3197-3203.

Gadala-Maria F. et al., Measurement of Fiber Orientation in Short-Fiber Compsites Using Digital Image Processing, Polymer Composites, US, vol. 14, No. 2, Apr. 1993, pp. 126-131.

U.S. Appl. No. 11/111,584, Shakespeare.

* cited by examiner

METHOD AND APPARATUS FOR MEASURING THE CREPE OF A MOVING SHEET

FIELD OF THE INVENTION

The present invention is directed to techniques of determining the spatial structure properties on webs and particularly to image-based measurements of the crepe structures on paper by on-line image analysis.

BACKGROUND OF THE INVENTION

In the manufacture of paper on continuous papermaking machines, a web of paper is formed from an aqueous suspension of fibers (stock) on a traveling mesh, papermaking fabric, or wire and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper.

In tissue making, the endless forming fabric is conveyed onto a turning Yankee dryer cylinder which is heated internally by steam to dry the web. A hood over the Yankee is supplied with the heated gases, often including combustion exhaust, which dry the web and remove the moisture evaporated therefrom. The dried web is detached from the Yankee cylinder by a doctor blade that extends across the width of the machine. This operation simultaneously crepes or crumples the web in the machine direction, so that micro-folds are formed, whose folding axis is substantially perpendicular to the machine axis. The creping does not impose single folds extending across the whole web, rather an apparently random pattern of interlaced and highly elongated branching folds each extending for distances of millimeters to centimeters across the machine, and with a distribution of folding pitches typically of some hundreds of microns. On the hood side, this folding gives the tissue surface a furrowed appearance of rolling relief, while on the cylinder side the folding tends to resemble a smoother surface of low relief crossed by narrow seams. The creped tissue is then conveyed with minimal contact of other apparatus to a reeling device. The mechanical and aerodynamic forces applied in conveying usually stretch the tissue by partial unfolding of the crepe, such that the crepe pitch is typically from 300-900 microns at the reeler. As is apparent, the quality of the tissue is determined in part by the creping operation on the tissue machine.

FIG. 1 is an image of the hood surface of a commercially available one-ply tissue which shows a network of ridges that are separated by furrows. One measure of the crepe pitch or crepe scale is to determine by the number of ridges or furrows per unit length along a linear path, e.g., line H, which is shown as being parallel with the machine direction. Most ridges, e.g., A, F and G, and furrows are essentially or nearly straight. Branching at various junctures, e.g., B, C, and E, occurs so that groups of ridges or furrows can be connected. The lengths, widths, and angles of individual ridges or furrows, or sections of connected ridges or furrows are distributed over some range of values.

The crepe pattern and especially the pitch of crepe folds or seams is an important product quality indicator for tissue. Crepe structure is related to properties of bulk, softness, and absorbency in tissue, which greatly influence its utility for a purpose, and customer satisfaction with tissue products. The crepe pattern is also an important process quality indicator for tissue-making machines. Deviations in crepe pattern either locally or across the whole sheet can indicate a range of process problems, such as excessive wear on the doctor blade, or improper flow of additives to the Yankee cylinder.

Timely information on crepe structure or changes in crepe structure allows the process to be promptly adjusted so that an acceptable product is made at all times. Such adjustments can include changing the angle or pressure of the doctor blade, or changing the amount and relative proportions or spatial distribution of water, glue, and other agents which are continuously applied to the Yankee cylinder surface. Moreover, knowledge of the crepe structure allows optimal scheduling of doctor blade changes, which is a costly operation requiring an interruption to production.

U.S. Pat. No. 5,654,799 to Chase et al. discloses a device for making very high speed measurements of the smoothness of a moving sheet such as paper; the patent purports that the apparatus, which employs an on-line laser triangulation position sensing system, can be used to infer the crepe wavelengths of tissue. However, in this mode of operation, the device requires that the tissue path be confined to a very narrow plane by a sheet stabilizer in the immediate vicinity where detection is made, which is problematic. Strict confinement of the web path would require either significant web tension or other direct mechanical forces, or substantial aerodynamic elements such as forced vortices or blowboxes which induce indirect tension. In any of these scenarios, the force applied can easily lead to decreping or even to web disruption, since most grades of tissue are not strong, and the crepe folds are only weakly bonded. The forces involved also increase nonlinearly with the speed of the web, thereby exacerbating the difficulty at the high speeds of modern tissue machines. Moreover, even if the mechanical difficulties could be overcome, measurement of crepe from surface roughness would be useful only on the hood side of the web, which is the surface of the tissue away from the Yankee cylinder. The reason is that the creping process is asymmetric which forms curved surface folds on the hood side and seams in an otherwise smoother surface on the cylinder side.

U.S. Patent Application 2005/0004956 to Pourdeyhimi discloses a method of evaluating surface texture in which surface features and defects of samples are said to be deduced by analyzing digitized images of illuminated surface. Specifically, the technique is directed to detecting selected surface and physical optical properties such as fiber orientation distribution and basis weight non-uniformity (blotchiness) of carpets. While the application states parenthetically that paper structures can also be evaluated, the reference provides no details to accomplish this. Moreover, that application teaches exclusively the use of two-dimensional Fourier analysis for its quantification of orientation distributions, whereas as will be disclosed below, with the present invention, analysis of crepe folding orientations is performed by a non-spectral method.

At present, there is no known method to measure the crepe structure until a sample can be taken from a finished reel to the laboratory for analysis. This leads to delays between the occurrence of a product quality disturbance or process defect and its detection. Thus remedial actions are delayed and considerable quantities of unacceptable tissue may be produced. The industry is in need of techniques for on-line crepe structure measurements with the goal of maintaining output quality and minimizing the quantity of product that must be rejected due to disturbances in the manufacturing process.

SUMMARY OF THE INVENTION

The present invention is based in part on the development of an image-based measurement technique that directly measures the crepe pattern orientation on a moving web that typically comprises non-woven material. The technique is capable of measuring a larger area of the web, e.g., paper, and thus produces a measurement which is more representative of the web. The invention is particularly suited for measuring the crepe structure of tissue during the manufacturing operation. A suitable arrangement of illumination, optical elements, and an imaging device obtain images of the tissue surface. The image resolution is sufficient to represent tissue crepe folds at the scale of the crepe. A spectral analysis of some or of all the images reveals the crepe folding pitch. Further analysis of the image optionally reveals other crepe structural parameters, such as the distribution of crepe fold orientation angles and distribution of linear fold lengths. Thus, changes in the crepe structure can be detected promptly, allowing corrective actions to be taken in a timely manner. Corrective actions can include (i) changing the doctor blade, (ii) adjustment of doctor blade angle, and (iii) adjustment of application of additives to the Yankee surface. Some corrective actions can be taken by a suitable control system which takes the crepe measurement as an input. The present invention provides a solution for measuring the crepe pitch and other crepe pattern parameters of a moving tissue web without the shortcomings of prior art.

In one embodiment, the invention is directed to a method for measuring the crepe pattern of a moving sheet that includes the steps of:

(a) illuminating an area on at least one side of the sheet with radiation;

(b) obtaining at least one digital image of the illuminated area; and (c) calculating the crepe pattern of the web by processing at least one digital image.

In another embodiment, the invention is directed to a sensor system for measuring the crepe pattern of a moving sheet that includes:

image obtaining means for obtaining at least one digital image of an illuminated area on the moving sheet; and control means for calculating the crepe pattern of the sheet by processing the at least one digital image.

In a further embodiment, the invention is directed to a method for measuring the crepe pattern of a moving sheet that includes the steps of:

(a) illuminating an area on at least one side of the sheet with radiation;

(b) obtaining at least one digital image of the illuminated area; and (c) calculating crepe folding of the sheet by processing at least one digital image with a gradient operator.

In operation, with the inventive apparatus, if the image provided by the lens and camera yields an image with a pixel scale corresponding to less than 100 microns of sheet, and the sheet has moved by less than half that distance during the image acquisition, then the image will represent features at the scale of the crepe structure. The image thus formed can be analyzed in any of several ways to produce a measurement of the crepe structure.

For example, a spectral decomposition is made of one or more sections through the image, where the sections are essentially aligned with the machine axis or direction of movement of the web, but the analysis need not necessarily employ the whole width of the image in that direction. Each such section through the image can be a single line of pixels, or an average or weighed combination of a plurality of lines of pixels. If a plurality of lines of pixels are averaged or combined, they need not necessarily be adjacent to one another, but it is advantageous if they are adjacent and form contiguous groups of lines of pixels A spectral decomposition of a section through the image is preferably obtained by a Fourier transform, or by a continuous or discrete wavelet transform, since these are numerically efficient. The Fourier method expresses the spectrum in terms of wavelengths of periodic structures, while wavelet methods express the spectrum in terms of aperiodic scales. However, other spectral decompositions can also be employed, such as the Hartley transform or the Wigner-Ville transform. These spectral decomposition techniques and their implementation, such as normalization of the spectrum or estimation of statistical confidence intervals, are standard methods in the fields of signal processing and image processing. The spectrum thus obtained comprises a set of factors indicating the amplitude or spectral energy at the wavelengths or scales used in the spectral analysis.

While satisfactory analysis of crepe may be achieved with any of a wide range of wavelet families, it is advantageous to employ a compact wavelet of high regularity in the wavelet-based spectral analysis. Lack of compactness increases the computational effort and also leads to undesirable edge effects being propagated further into the spectrum, while lack of regularity leads to poor localization in the frequency domain. Another desirable quality is simple symmetry, such as being symmetrical or antisymmetrical, which leads to spectra which are easier for a non-expert to interpret. Thus, standard wavelets which are suitable include (i) Daubechies wavelets of fourth or higher order which provide maximal compactness and regularity but are very unsymmetric, (ii) Coiflet wavelets which provide high compactness and regularity and are nearly symmetric, and (iii) biorthogonal wavelets which provide adequate compactness and regularity with simple symmetry characteristics.

It is also possible to use wavelets which are not particularly compact but have adequate regularity, such as the discrete Meyer wavelet. However, this is less advantageous since to produce results comparable to those obtained with a compact regular wavelet it would be necessary to use a larger number of pixels in the analysis, i.e., from a larger image, and to perform a greater number of computational operations.

Wavelet-lifting or other commonly-known design methods can be used to derive nonstandard wavelets of suitable properties from known functions. For instance, wavelet functions having only integer coefficients can be produced in this way, resulting in great computational economy and speed when applied to integer-valued image pixel data.

Spectral analysis using the Wigner-Ville transform, i.e., forming the Wigner distribution of the data, provides the additional advantage that the spectrum is localized in position analogously to the wavelet methods, but the spectral coefficients at each location can be interpreted directly as spatial frequencies just as in a Fourier spectrum. Thus, the Wigner distribution contains instantaneous spectra for each location in the data, combining the strengths of both Fourier and wavelet methods. This advantage comes at the cost of additional computation, greatly exceeding the computational effort needed for Fourier or wavelet spectral analyses.

As is apparent, if spectral decompositions are obtained for a plurality of sections which are separated by only small distances, the spectra can be combined to form a composite that is representative of a larger area than the spectrum of any single section. This result will, in general, differ from the spectrum which would be obtained by combining all of the plurality of sections and computing a single spectrum therefrom. Similarly, this spectra combination can be performed using spectra from sections which are not all in the same image. Thus, the spectra can be representative of (i) longer time scales, by combining data from images at substantially the same location at different times or (ii) larger regions of the web, by combining data from a plurality of images at different locations.

Having obtained a suitable spectrum that is representative of a selected region of the web over a desired time interval, the crepe pitch and other parameters can be inferred. Each peak or local maximum in the spectrum corresponds to a prominent wavelength or scale of features in the web images. Since the spectrum intensity is determined by the illumination and surface geometry, most spectral features will correspond to surface features on the web, but some long-wave or long-scale spectral features may correspond to irregularities in the illumination or deviations in the path of the moving tissue. It is therefore advantageous to preprocess or reduce the spectrum before subsequent processing, for instance by excluding features or spectral bands which are known to be unrelated to the crepe structure. The dominant surface feature on tissue after creping is the crepe itself, whether observed on the hood side or the cylinder side. This results in a range of prominent wavelengths or scales in the spectrum, and the crepe pitch or crepe scale can be directly inferred from the wavelength or scale of such a spectral feature.

The absence of a prominent spectral peak in or close to the expected wavelength or scale is an indicator that the creping process is seriously amiss. Similarly, shifts in the wavelength or scale can signal changes in the process which may require corrective action, depending on whether they are within the acceptable range. The degree of prominence of the spectral peak is also a valuable indicator of the health of the creping process and the quality of the creped tissue, as it is related to the depth of the folds or seams that are visible on the web surface.

While the pitch of creping is the principal parameter for describing the crepe pattern, the present invention also provides techniques for further characterization of the crepe pattern. In particular, these techniques can be used to determine the distribution of angles of the crepe furrows on the hood side or equivalently of the crepe seams on the cylinder side. The image scale used determines the scale of the features whose orientations are measured by a differintegral operator.

Similarly, by performing spectral analysis of sections that are orthogonal to the machine axis or orthogonal to the direction of movement of the web, it is possible to characterize the distribution of crepe folding lengths in the cross-machine direction. This corresponds to both the distribution of furrow lengths on the hood side and the distribution of seam lengths on the cylinder side. This measurement is preferably made on the hood side due to the enhanced feature relief; moreover, the fact that furrows are wider than seams makes the measurement more robust on the hood side.

In another aspect of the invention, the image-based measurement techniques can be employed to estimate the crepe fold orientation by analyzing digital images using gradient-type operators in at least two preferably orthogonal axes at a plurality of loci in the digital images.

DETAILED DESCRIPTION OF THE PREFERRED EMBODIMENTS

Figure 1:
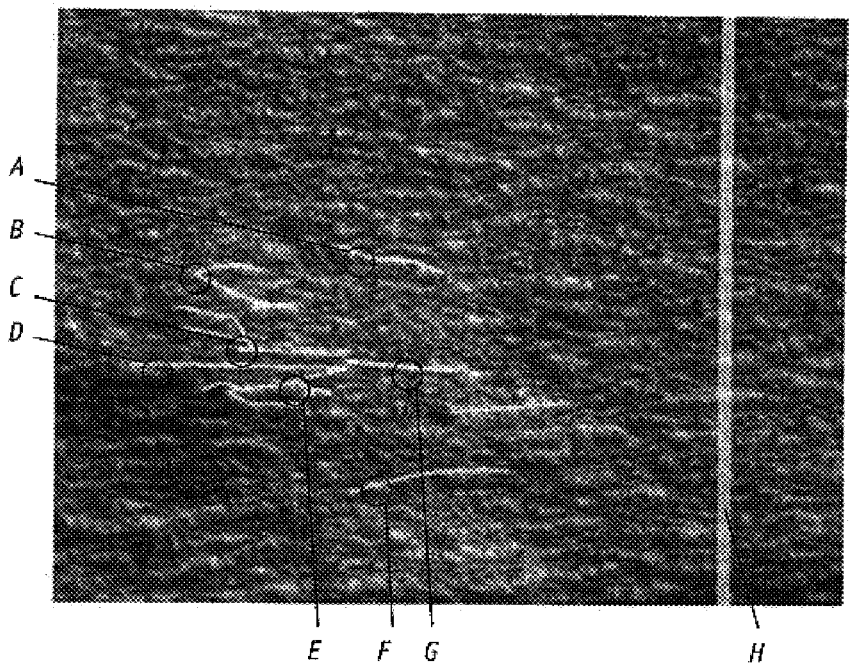
FIG. 1 is a real-time image of crepe patterns on a tissue surface.
Figure 2:
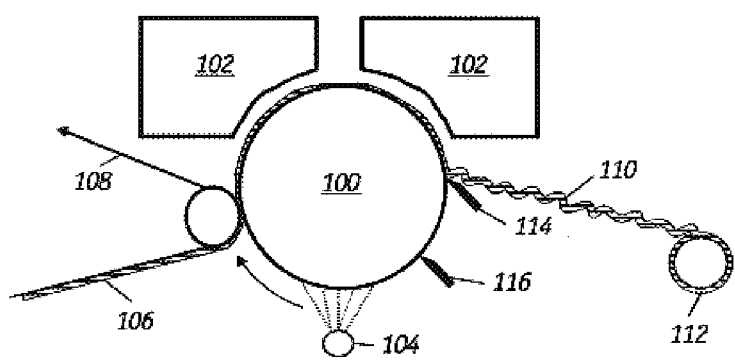
FIG. 2 is a cross-section of a Yankee cylinder.

The present invention relates to methods and devices for directly measuring the crepe pattern and related structures or features on the surface of a moving sheet or web product such as tissue during the manufacturing operation. FIG. 2 illustrates a typical tissue creping process whereby non-creped sheet 106 is conveyed by a continuous felt line 108 to the surface of a rotating Yankee drying cylinder 100. Dryer hoods 102 apply heat that is directed to the upper or hood side surface of the sheet. The addition of an adhesive material from a spray boom 104 onto the cylinder surface helps keep sheet 106 adhered to the cylinder. The sheet becomes creped sheet 110 as it is scraped off the cylinder surface by the doctor blade 114. The cleaning blade 116 removes excess materials from the surface. The crepe pattern of creped sheet 110 can be monitored by positioning the inventive measuring apparatus between the Yankee cylinder 100 and reel 112. The crepe pattern on the creped sheet 110 can also be controlled to some extent by controlling the amount of adhesive that is sprayed and/or by controlling the angle that the tip of the doctor blade makes with the cylinder surface.

The cross-sectional structure of the creped sheet 110 is exaggerated for illustrative purposes. As is apparent, the creped sheet can be defined by at least two thicknesses; the first is the true, inherent thickness of sheet itself which is fairly constant regardless of the degree of creping. The second is the maximum distance between the tops of the ridges or peaks and the bottoms of the furrows or valleys of the creped sheet. The latter thickness or measurement, which is illustrated as a vertical distance relative to the plane of the moving creped sheet 110 in FIG. 2, is commonly referred to as the caliper. The creped sheet has a pattern of undulating folds that are imparted by the doctor blade 114. The axis of each fold is generally transverse to the machine direction in which in the creped sheet moves. The pitch of the folds, i.e., the folding pitch, is defined as the distance between two corresponding points on the undulating pattern. Typically, it is measured along a horizontal path between two adjacent peaks or ridges in the pattern. With the present invention, by aggregating measurements at multiple areas on the moving creped sheet either in the CD, MD or both CD and MD, composite crepe pattern information including (i) average folding pitch, (ii) distribution of folding pitches, (iii) average folding length, (iv) distribution of folding lengths, (iv) distribution of folding angles can be ascertained, and (v) other related features.

As an illustration, with an illumination pulse of 500 nanoseconds to freeze the image and with an image scale of 75 microns, the invention is capable of measuring crepe pitches in the normal range, i.e., exceeding 300 microns, on a moving sheet that travels at a rate of up to about 75 meters/sec. Tissue downstream from a Yankee cylinder typically travels at less than 35 meters/sec on modem machines.

As used herein, and unless specified otherwise, the term sheet or web refers generally to any type of paper sheet, e.g., tissue, towel facial, bath or a heavier basis weight product, creped or uncreped, blended, multilayer, i.e., with two or more layers, or single layered, and multiplied or singleplied. Similarly, as used herein, the term tissue refers to all types of lower basis weight soft and absorbent paper sheets, including without limitation bath or toilet tissue and facial tissue.

Figure 3:
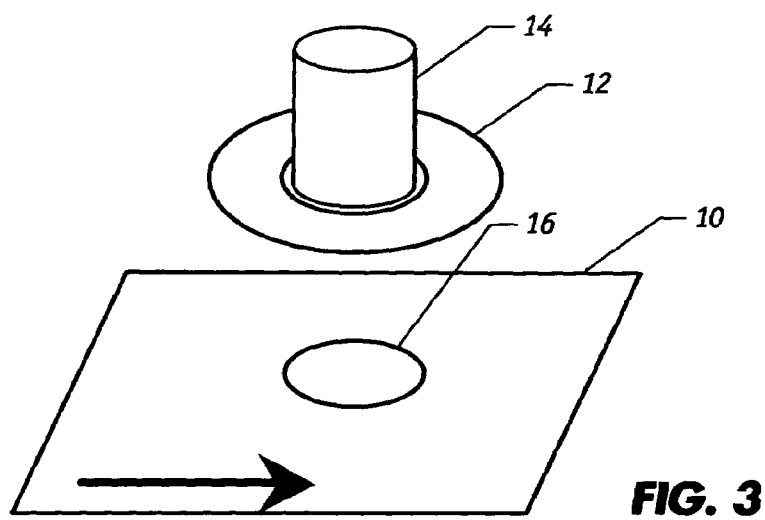
FIG. 3 illustrates crepe pattern measurements by on-line image analysis whereby the illumination source and imaging device are positioned on the same side of the moving web.

As shown in FIG. 3, an apparatus for measuring crepe pattern of a moving web 10 or sheet of paper includes an imaging device 14 and an annular light source 12 that are both positioned above the web 10. The imaging device 14 is typically a camera that is equipped with appropriate optics, e.g., lenses, to focus light that is reflected from the image area 16 into the camera. In this reflective mode configuration, surface images of the moving web 10 are derived from light that is reflected from the surface. The reflective mode of operation is particularly suited for measuring crepe pattern of web comprising a layer of opaque material or a web that is supported underneath by a fabric, wire or other structure that interferes with the transmission of light. Light from the light source 12 is directed toward the web 10 to illuminate an area on the surface and the imaging device 14 detects images from an image area 16 which is within the illuminated area. Although the size of the illumination area is not critical, it preferably is large enough to permit the imaging device 14 to image an area 16 that is at least about 25 mm$^2$ and is typically from 100 mm$^2$ to 1000 mm$^2$ in size. As is apparent, the larger the image area 16 on the web, the more representative is the crepe pattern that is measured.

The imaging device 14 and light source 12 are configured so that the image scale is sufficient to allow crepe features in the moving web 10 to be discerned. Thus, imaging detectors, e.g., cameras, suitable for use as the imaging device 14 should have pixel sizes that do not exceed one quarter of the typical width of a single crepe feature or structure. This corresponds to about 75-100 microns per pixel in the imaging detector when using adequate lenses.

Conventional lenses can be employed with the camera when the moving web 10 is stable so that its distance from the imaging device 14 is relatively constant which is applicable when the web 10 is adequately supported. However, if aerodynamic effects cause the moving web 10 to flutter or otherwise shift its vertical position relative to the imaging device 14, a telecentric lens system that creates a large depth of field can be used so that fluctuations of the web 10 relative to the camera results in no change in image size. In any event, with the present invention no stabilizer to constrain the moving sheet to a very narrow path is required.

When the light source 12 is located on the same side as the imaging device 14 as shown in FIG. 3, the illumination is preferably symmetrical around the optical axis of the imaging device 14. For instance, an annular-shaped light source 12 where the illumination from the light source 12 to the web 10 is directional, typically at an angle that is from about 30° to 75° to normal, can be employed. Light sources that produce illumination having angles outside this range can also be used, but less uniform image weighing to each crepe pattern is achieved. Alternatively, light sources that generate multiple beams of light with multiple angles of illumination can be employed. As further described herein, the illumination can be derived from an array of light sources that are distributed in one or more concentric annuli such that the illumination is substantially symmetrical around their common axis. Different light beams can be directed at the web 10 either simultaneously or sequentially. The illumination can be monochrome or polychrome and the character of illumination can differ between illumination angles. Although the wavelength of the radiation is not critical, ultraviolet, or visible, and especially near-infrared radiation is preferred for measuring crepe pattern on paper.

In the case where the web of material being monitored contains an appreciable amount of water or non-fibrous material such as resins, fillers or sizing starch, imaging at different wavelength ranges can allow for better discrimination between the fibrous and non-fibrous materials. The apparatus can comprise a light source 12 such a quartz tungsten halogen (QTH) lamp that supplies a broadband infrared radiation and one or more detectors with the wavelength of interest being selected by a narrow-band filter, for example, an interference type filter. The images can be obtained, for instance, by prismatic or partial-mirror separation into multiple images of the same illuminated area. In particular, fluorescence can be advantageously used, whereby the wavelength range of measurement for one image is in the fluorescence emission band, and illumination is at low intensity in that band, but high intensity in the fluorescence excitation band.

The concept is to take advantage of fluorescent agents already present in some paper for any of several purposes: (i) to help distinguish between fiber and non-fiber constituents, (ii) to help distinguish between surface and subsurface fibers, or (iii) to boost the amount of light which forms the image on the detector. It is understood that a fluorescent agent can be added explicitly to facilitate measurement.

Many grades of paper include fluorescent agents to enhance their perceived color. For example, fluorescent brightening agents (such as Tinopal UP) are usually present in office paper, e.g., photocopy/laser/inkjet, and are often used in other white grades. The excitation band for these agents is typically from 330 nm to 410 nm with emission from 380 nm to 500 nm. Thus they boost the blue content of remitted light when the illumination contains some ultraviolet. This makes the paper appear brighter as the remitted light is boosted overall, and makes it look whiter as it counters the intrinsic yellow cast of lignin in cellulose fibers which have not been completely bleached.

Some specialty grades use other fluorescent agents. For example, very intense colors can be achieved by using fluorescent dyes. These work in a similar fashion to fluorescent brighteners, except that the fluorescent excitation and emission bands are shifted. For example, Fastusol Yellow 14L has fluorescent excitation in blue centered at 450 nm and emission in green centered at 510 nm. Fluorescent agents having particular excitation and emission behavior are often used in security papers, such as currency or other financial instruments, and in stock certificates, commercial bonds, etc.

Fluorescent brightening agents are normally dosed into the stock stream and are thus adsorbed onto the fibers before filler material is introduced. If the paper is illuminated primarily with ultraviolet (UV-A), then an image formed using blue light will be predominantly fluorescent emission from the fibers. The fillers may absorb or scatter the ultraviolet light, but they will not contribute much to the fluorescent emission in blue.

In a multilayer sheet, fluorescent brightening agents are introduced mostly into the surface layers. This is where they have the most effect, and since they tend to be expensive, dosing them into the interior layers would not be economic. Even in a single layer sheet, ultraviolet light tends to penetrate less into the sheet than visible light, due to scattering effects. Thus, the crepe pattern inferred from a visible light image formed with visible light illumination, and the crepe pattern inferred from a blue light image formed with ultraviolet illumination may differ.

If the sheet is illuminated with a rich light source, i.e., one which includes both UV and visible light, then fluorescence will boost the intensity of an image received by a detector sensitive to visible light.

Diffuse illumination can also be used, especially if aerodynamic effects are small and the web 10 does not flutter. Diffuse illumination can be created by positioning a diffuser in the light path. Diffuse lighting can be created by reflecting light from a light source off one or more reflective surfaces that provide for non-directional and softer illumination.

The light source 12 preferably provides high intensity illumination that consists of a constant stream of energy within a wavelength required for measurement. The light source 12 can be amplitude modulated by conventional mechanical devices such as choppers, shutters, tuning forks and the like to enhance the signal-to-noise ratio. Another exemplary modulating technique employs electro-optical shutters such as Kerr cells and Pockels cells that are positioned in the light beam path of the light source and acousto-optical devices such as acousto-optical tunable filters. Alternatively, direct modulation of a drive current that is coupled to the light source to generate pulsed illumination can be used.

Preferred light source devices include light-emitting diode (LED), laser diode, or an array of LEDs or laser diodes. When the light source is modulated to create a stroboscopic flash effect, for instance, a high modulation rate is preferred. The resulting short exposure times allow the imaging device 14, with correspondingly short integration times, to obtain better images of the image area 16 by reducing or eliminating the adverse effects caused by motion-blurring in the direction of movement of the web 10. In the case of a charge-coupled device (CCD), a short integration time lets pixels collect less light and a longer integration time lets pixels collect more light. Alternatively, or in addition to modulating the light source, the imaging device 14, e.g., CCD array camera or CMOS array camera, that operates at a high exposure rates, i.e., short integration times, can be selected. In this case, the illumination can be continuous which makes it is easier to maintain consistent illumination at different measurements.

The image scale of the image formed on the detector preferably corresponds to the expected range of crepe features to be measured. For instance, if the crepe pitch to be measured is not less than 300 microns, then the image scale is preferably not more than 75 microns per detector pixel. If the pixels correspond to larger scales, then the accuracy of crepe measurement may be degraded.

On the other hand, while it is desirable to have pixels which correspond to smaller image scales to improve spectral accuracy, there are also disadvantages in having pixels which are too small in image scale. For example, the detector sensitivity must be higher for pixels of small image scales. Also, the number of pixels required to represent a given number of crepe folds is greater, so that spectral or other analysis requires more computation. Moreover, the determination of folding angle distribution can be biased by presence of features narrower than crepe folds if the image scale for each pixel is too small. If the image scale is considerably less than the required value, then the image can be transformed to a more suitable scale before it is analyzed, for instance, by a two-dimensional averaging and re-sampling. Alternatively, pixel-binning directly on the detector may be used to provide fewer pixels corresponding to larger scale in the image.

Crepe pattern information is derived by spectral analysis of images of the moving sheet surface. A preferred method of continuously analyzing a moving tissue employs, designated as Method I, applies line analysis to linear sections of an array images to measure crepe properties. Method I employs the followings steps:

Step 1. An area of a moving sheet is illuminated and an image of the illuminated area is generated. The illumination is preferably created by directing radiation from an annulus or disk which is coaxial with the optics which captures the image of the sheet. The illumination is preferably uniform across the imaged area and of equal intensity from each direction; moreover, the illumination is preferably stroboscopic with a pulse length that is short enough such that the distance traveled by the sheet during the light pulse interval is less than one quarter of the expected distance between neighboring crepe folds on the sheet.

Step 2. The optical image of the illuminated area is recorded in digital form, preferably with a CCD or CMOS array camera. Optionally, wavelength selective filters may be used so that only some wavelengths of the optical image are recorded. The pixel elements of the image are preferably in a rectilinear array, of which one axis is parallel to the direction of sheet movement, such that the columns of the image are aligned with the direction of sheet movement. If the illumination in step 1 is continuous, the camera exposure time is most preferably short enough so that the distance traveled by the sheet during the exposure time is less than one quarter the expected distance between neighboring crepe folds on the sheet.

Step 3. At least one section of the image that is parallel to the direction of sheet movement is extracted from the image. These sections preferably comprise averages or weighted averages of a plurality of adjacent columns of pixels. Each of these columns of pixels or the average section formed from them can optionally be filtered in the direction of the sheet movement to attenuate or enhance specific features or spectral properties.

Step 4. Each extracted section is spectrally decomposed to form a spectrum. The spectral decomposition preferably employs a Fourier or Wavelet or Wigner-Ville basis. The spectrum can be filtered or abridged if desired. Optionally, an average spectrum is formed from the spectra that are computed individually from a plurality of sections, and this average spectrum is subtracted from the spectrum of each extracted section thereby forming a reduced spectrum.

Step 5. One or more peaks are located in the spectrum or reduced spectrum for each extracted section and each peak is quantified as (i) the wavelength or scale of the peak, (ii) the amplitude of the peak, and (iii) a dispersion factor or spectral width factor of the peak. A significance metric of each peak is computed as the product of its amplitude times its dispersion factor or spectral width factor.

Step 6. The primary crepe pitch is calculated from the wavelength or scale of the peak with the greatest significance metric. Optionally, secondary and other peaks, if they exist, are similarly evaluated and ranked.

The distribution of orientations of crepe folds can also be determined from the image measurements by using fractional order differintegral gradient techniques as further described herein. This information is also of diagnostic value in making tissue as it reveals changes in the creping process and provides additional quality parameters of the creped tissue.

A second preferred method of continuously analyzing a moving tissue, which is designated Method II, preferably uses a linear image from a line camera. Method II employs the following steps:

Step 1. An area of the moving sheet is illuminated and an image of the illuminated area is formed. The illumination is uniform in direction and intensity along the image. The illumination is preferably stroboscopic with a pulse length short enough that the distance moved by the sheet during the light pulse is less than one quarter the expected distance between neighboring crepe folds on the sheet.

Step 2. The optical image of the illuminated area is recorded in digital form, preferably by means of a CCD line camera or CMOS line camera. Optionally, wavelength selective filters may be used so that only some wavelengths of the optical image are recorded. The pixel elements of the image are preferably arranged in a linear array, of which the linear axis is parallel to the direction of sheet movement, such that the linear image is aligned with the direction of sheet movement. Optionally, the pixel elements may form a multilinear array which comprises plural linear arrays, each aligned in the direction of movement of the sheet. If the illumination in step 1 is continuous, the camera exposure time is most preferably short enough that the distance moved by the sheet during the exposure is less than one quarter the expected distance between neighboring crepe folds on the sheet.

Step 3. The linear image is spectrally decomposed to form a spectrum. The spectral decomposition preferably employs a Fourier or Wavelet or Wigner-Ville basis. Optionally, a filtering can be performed before the spectral decomposition to attenuate or enhance specific features or spectral properties. Optionally, the spectrum can be filtered or abridged, or a reference spectrum can be subtracted.

Step 4. One or more peaks are located in the resulting spectrum and each peak is quantified as (i) the wavelength or scale of the peak, (ii) the amplitude of the peak, and (iii) a dispersion factor or spectral width factor of the peak. A significance metric of each peak is computed as the product of its amplitude times its dispersion factor or spectral width factor.

Step 5. The primary crepe pitch is calculated from the wavelength or scale of the peak with the greatest significance. Optionally, secondary and other peaks, if they exist, are similarly evaluated and ranked.

For Methods I and II, the illumination is preferably from the same side of the sheet as the imaging. In Method 1, for instance, an annular illumination is used if illumination and imaging are on the same side of the sheet. However, if illumination is on the opposite side, it can employ either a disk source or an annular source.

The line camera imaging and line image analysis of Method II can use annular or disk illumination as in Method I. However, the technique of Method II does not require such sophisticated illumination arrangements, and can employ instead any geometry of illumination which provides light of essentially the same intensity and direction at each point along the imaged line. Examples include (i) a uniform collimated sheet of light of adequate thickness from one direction illuminating the line to be imaged, (ii) plural uniform sheets of light each illuminating the imaged line from different directions (iii) diffuse light uniformly illuminating the line to be imaged.

The light pulse length most preferably is quite short, typically from sub-microsecond to a few microseconds in duration, depending on the speed of movement of the sheet and the expected range of crepe folding pitches. Thus, Xenon strobes can be used only for the slower speeds with longer crepe folds, as the Xenon discharge arc has an intrinsic life of more than 6 microseconds.

For both Methods I and II, the preferred illumination device is a set of LED elements in a suitable geometric arrangement, equipped with a fast-switching power supply. LEDs can deliver high intensity pulses as short as 100 nanoseconds, and can be arranged to deliver light with freely specifiable geometry, such as the uniform annular illumination preferred for Method I. They can also be used to deliver uniform sheets of light which is the preferred technique in Method II.

Laser strobes are an alternative light source, which can deliver even shorter pulses than LEDs while maintaining comparable total light energy levels. Achieving the desired illumination geometry is more difficult with a laser strobe, nevertheless, by incorporating expansion lenses or mirrors, a laser strobe can deliver a uniform sheet of collimated light which is particularly suited for use in Method II. Moreover, when equipped with beam splitters and other optics, a laser can deliver multiple sheets of collimated or diffused light with different incidence angles. With appropriately designed optical arrangements, such as a plurality of mirrors, lenses, splitters, fibers, and the like, laser strobes can also deliver more complicated illumination geometries, such as annular illumination.

Use of continuous illumination with short-exposure cameras is also possible, provided the exposure can be set short enough. Microsecond level exposures are possible with some commercially available devices. However, the illumination intensity required can lead to thermal problems or unacceptable energy consumption. This approach may be feasible for illumination in some cases, such as illumination focused from a distance.

For either Method I or II, the measurement device is preferably in a traversing apparatus which sequentially measures the whole sheet width. Alternatively, an array of the devices can be deployed across the machine such that the whole sheet width is measured essentially simultaneously.

Figure 4:
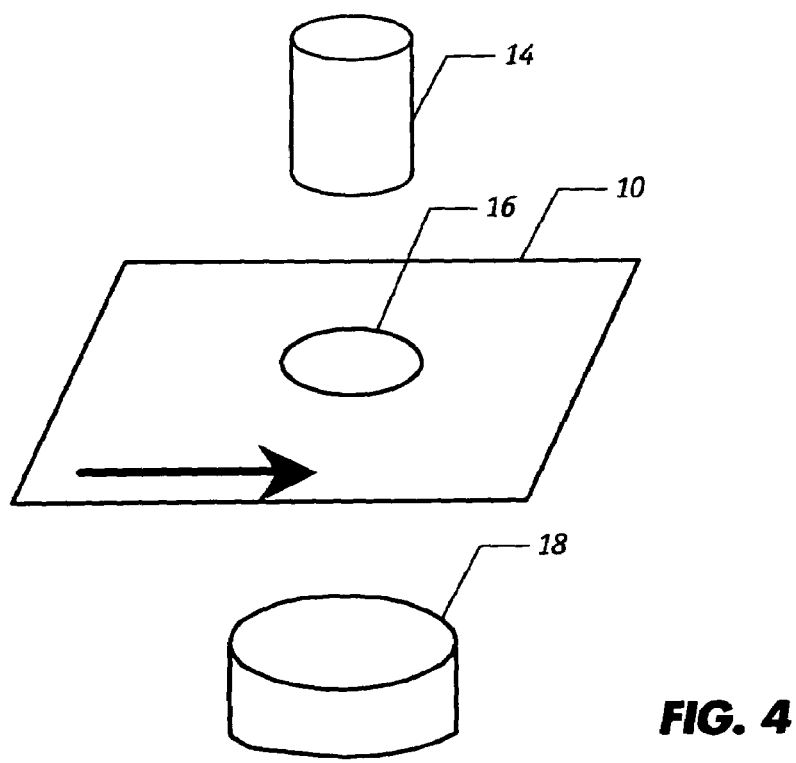
FIG. 4 illustrates crepe pattern measurements by on-line image analysis whereby the illumination source and imaging device are positioned on opposite sides of the moving web.

FIG. 4 illustrates the transmissive mode of operation for measuring crepe pattern of a moving web 10 or sheet of paper. This configuration is particularly suited for monitoring an unsupported, non-opaque web. Indeed, when the web is non-opaque and is not supported by a wire or other structure, both reflective and transmissive modes of operation can be employed. As shown, the apparatus includes a light source 18 and imaging device 14 that are positioned on opposite sides of the web 10. The intensity of the light from the light source 18 must be high enough to transmit through the thickness of the web 10 to illuminate the upper surface of the web 10 for images of the image area 16 to be focused into the imaging device 14, e.g., camera. The light source 18 can be positioned directly below the imaging device to provide directional illumination that is perpendicular to the web. Alternatively, the light source 18 can have an annular shape or other configuration for directional illumination that is symmetric around the optical axis of the imaging device 14.

Figure 5:
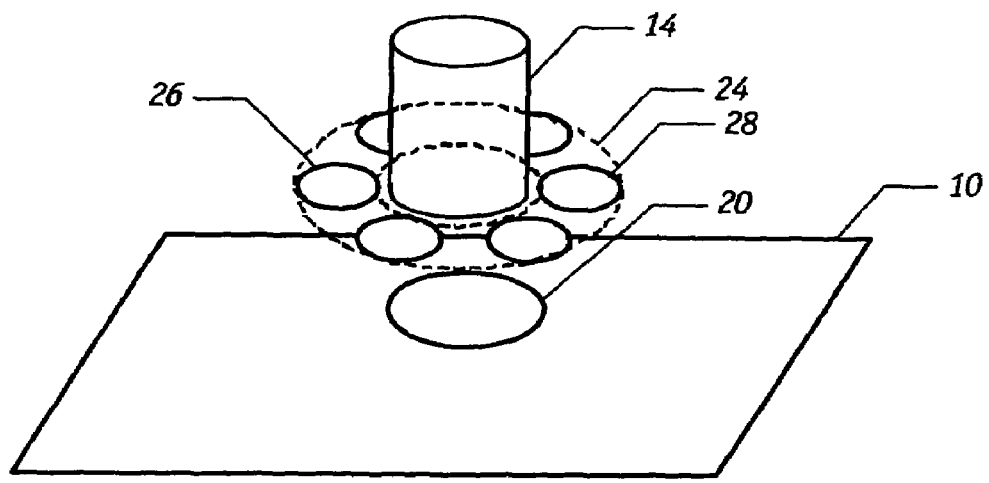
FIGS. 5 and 6 illustrate crepe pattern measurements by on-line image analysis whereby the illumination is an annulus of light sources which is on the same side of the moving web as the imaging device.

FIG. 5 illustrates another reflective mode configuration for crepe pattern measurements of a moving web 10 that includes an imaging device 14 and an annular light source 24 that illuminates area 20 on the web 10. The light source 24 includes a set of light sources 24, 26, and 28, for example, which are distributed along a concentric annulus such that the directional illumination is substantially symmetrical around the axis.

Figure 6:
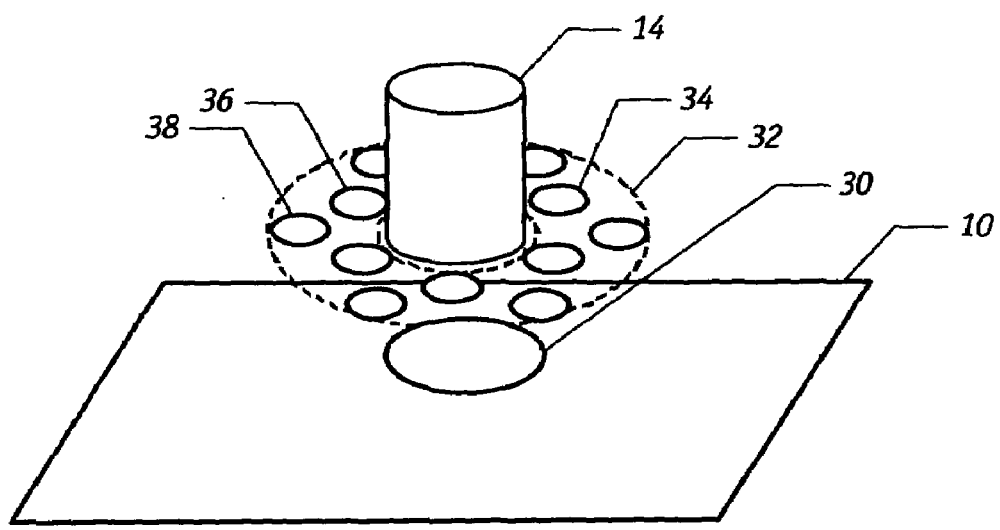

FIG. 6 illustrates a further reflection mode configuration for measurements of a moving web 10 that includes imaging device 14 and an annular light source 32 that illuminates area 30 on the web 10. The light source includes a set of light sources 34, 36, and 38, for example, which are distributed in two concentric annuli such that the directional illumination is substantially symmetrical around their common axis.

Figure 7:
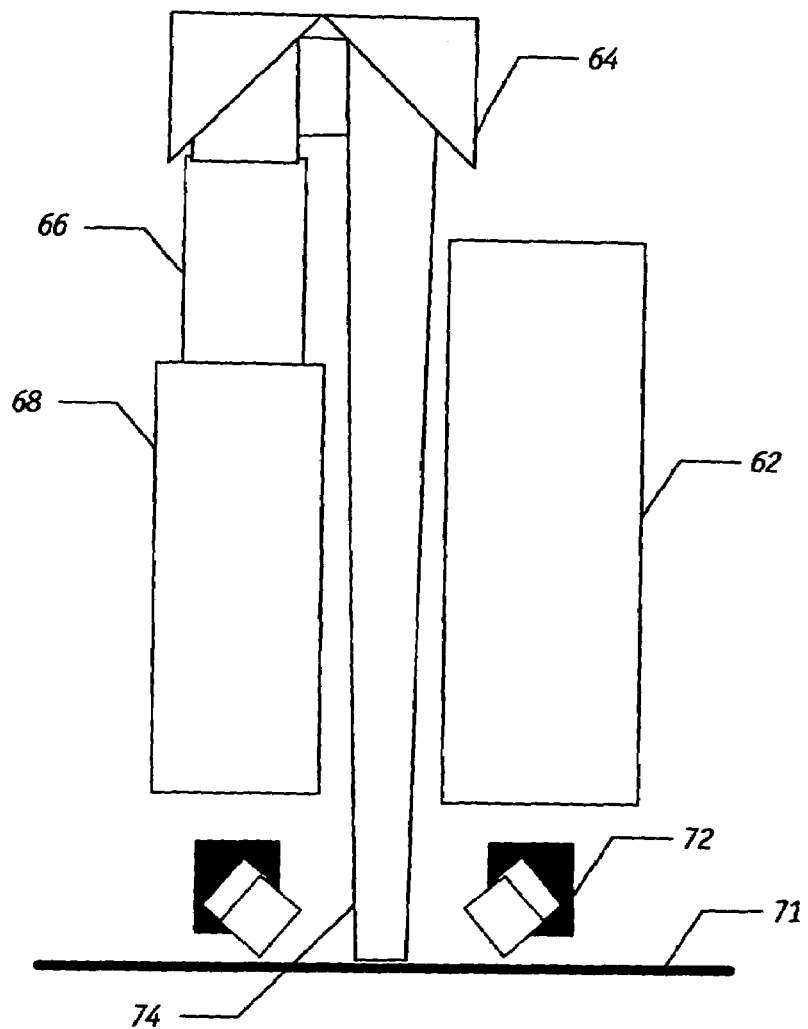
FIGS. 7 and 8 illustrate two embodiments of the inventive apparatus.

FIG. 7 is the cross sectional view of an apparatus for measurements operating in the reflective mode. The light source 72 is a LED ringlight that is positioned about 10 mm from the moving paper 71. A DC LED strobe controller 62 controls the light source 72 to generate strobing illumination for imaging the fast-moving web 71. A suitable strobe controller is the model S4000 by Advanced Illumination (Rochester, Vt.). A camera 68 is a charge-coupled device model XCD-X710 from Sony Corp. (New York, N.Y.). Light 74 reflecting from the paper 71 is directed by optically flat mirrors 64 into a very high resolution 50 mm lens 66 that is coupled to the camera 68. In one embodiment, the optics is configured so that the camera focuses down on an illumination spot on the surface of the web that is 10 to 15mm in diameter.

Figure 8:
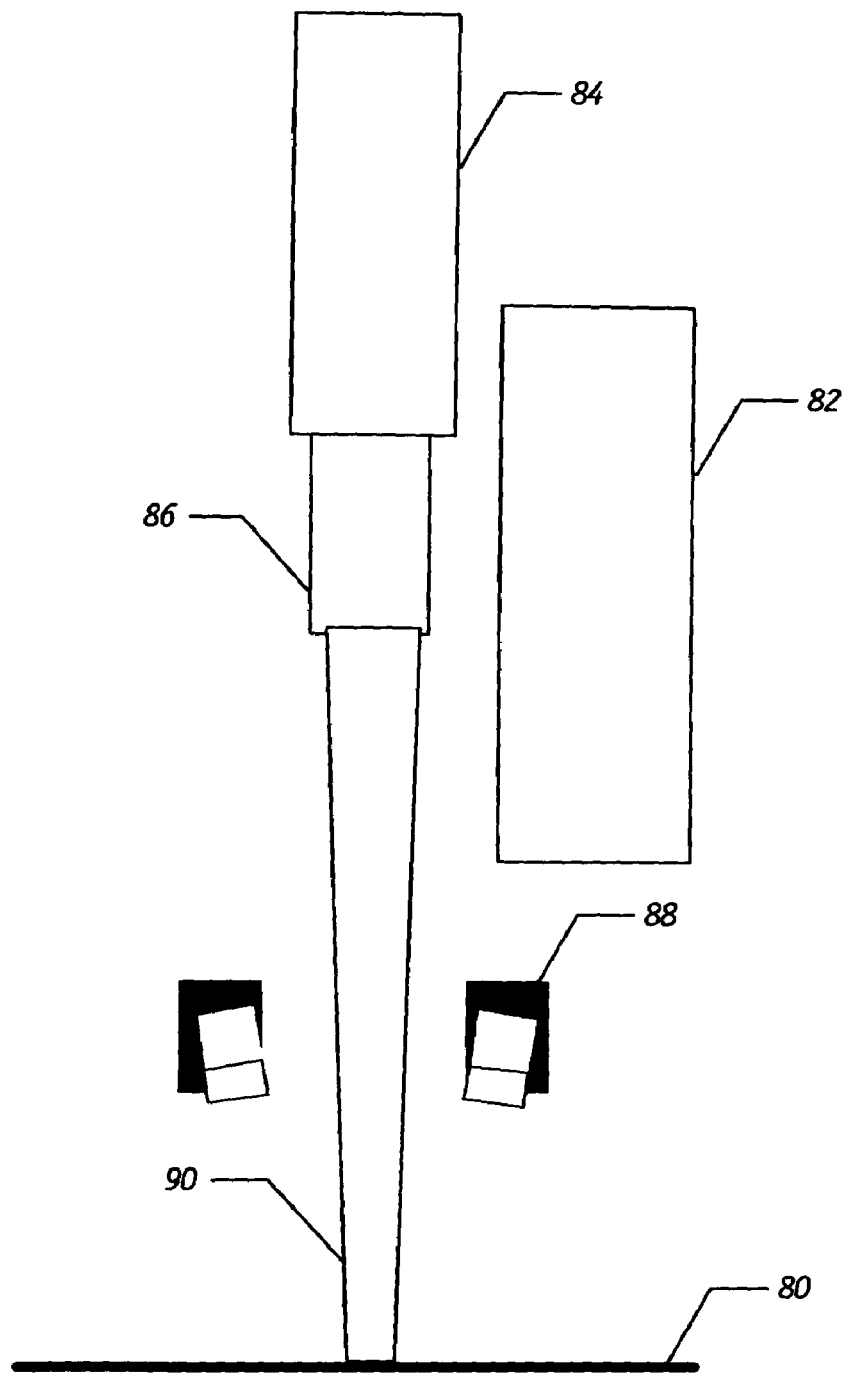

FIG. 8 is the cross sectional view of another apparatus for measurements operating in reflection mode. The light source 88 is a LED ringlight that is positioned about 75 mm from the moving paper 80. A DC LED strobe controller 82 controls the light source 88 to generate strobing illumination for imaging the fast-moving web 80. Light 90 reflecting from the paper 80 is captured by a charge-coupled device camera 84 through a very high resolution 50 mm lens.

Figure 9:
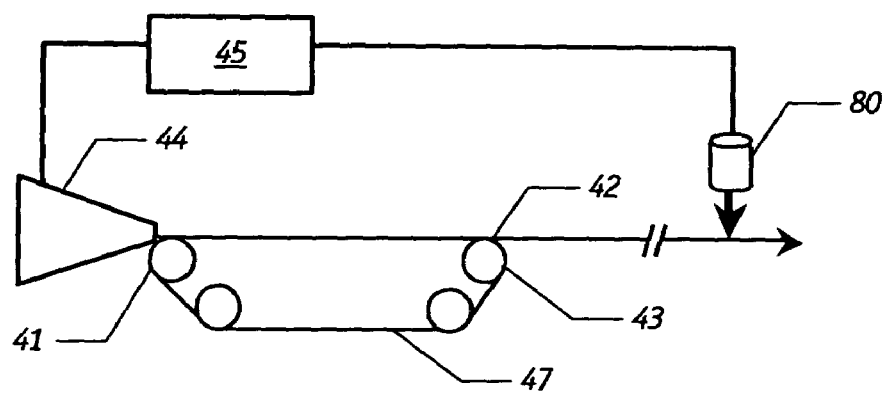
FIG. 9 illustrates deployment of the inventive crepe pattern measurement apparatus in a papermaking machine.

The invention can be used to measure the crepe pattern at strategic locations throughout the papermaking process especially between the Yankee cylinder and the reel where tissue is wounded. Continuously monitoring the crepe structure of the sheet allows corrective actions to be taken by a control system whenever the crepe starts to deviate from a desired state. FIG. 9 shows a portion of a typical sheetmaking system for producing a continuous sheet of paper material 42 that has a plurality of actuators that are arranged to control discharge of wet stock from a headbox 44 onto a supporting fourdrinier wire 47 along the cross direction (CD) which is transverse to the machine direction (MD) of the moving paper material 42. The paper material 42, which is a sheet of fibrous slurry that forms on top of the wire 47, is trained to travel in the MD between the rollers 41 and 43 and thereafter passes through a drying section that includes a Yankee cylinder (not shown). The portion of the papermaking process near the headbox 44 is commonly referred to as the "wet end," while the portion of the process near a take-up reel is referred to as the "dry end". As illustrated, the imaging device and light source components of the inventive apparatus, which are collectively depicted as device 80, are deployed in the reflective mode to measure the crepe pattern on the hood side of the sheet 42.

The inventive crepe pattern measurement apparatus further includes a computer 45 that is connected to an imaging device component of device 80 and actuators of the headbox 44 and other devices as further described herein. The computer 45 analyzes the digital images from the imaging device to estimate the crepe pattern of the paper 42 as further discussed herein. In addition, the computer includes a profile analyzer which includes a control system that operates in response to the cross-directional measurements from device 80. In operation, device 80 can be scanned in the cross direction to provide the computer 45 with digital images of the paper along the cross direction. From these images, signals that are indicative of the crepe pattern at various cross-directional measurement points are generated. The profile analyzer also includes software for controlling the operation of various components of the sheetmaking system, including, for example, the above described actuators of the headbox 44. Depending on the degree of deviation of the crepe pattern from a desired set point or target, wet end and/or dry end parameters can be adjusted accordingly to change the crepe pattern. For example, the crepe pattern in tissue can be altered by changing the amount of water or chemicals in the feedstock. Thus, flow of water and other components of the feedstock can be manipulated in order to control the crepe pattern.

Computer 45 can also be designed to adjust the operations of the Yankee cylinder that is illustrated in FIG. 2. Additional corrective actions include (i) changing the flow of additives applied to the surface of the Yankee cylinder through the spray boom, either locally or across the whole machine, (ii) adjusting the angle or pressure of the doctor blade, either locally or across the whole device, and (iii) changing the steam pressure in the Yankee cylinder or changing the temperature or flow of heated gasses in the hood. The control system can be a cross-directional profile controller or a machine direction controller, or a combined CD and MD controller. Similarly, the controller may control only the crepe, or it may control crepe and other parameters such as an optimization-based control, for instance.

By monitoring the creping process, it is possible to optimally schedule changes of the doctor blade. It can be replaced in a timely fashion, as soon as some part of the blade approaches or reaches the end of its useful service life, neither sooner nor later. Since wear of the doctor blade is uneven across the machine and varies from time to time according to operating conditions, the useful service life of a doctor blade cannot be accurately predicted. Replacing the doctor blade is costly, as it requires an interruption to production as well as the intrinsic cost of the doctor blade. If the doctor blade is replaced while it still has some useful service life remaining, the cost in lost production and consumption of blades is unnecessarily high. However, if a doctor blade is used after part of it is worn out, then there is an unnecessary high cost from production of unacceptable products and consequent wasted energy and consumable materials.

As is apparent, the present invention provides a method of on-line measuring the crepe pattern of a moving web by analyzing digital images thereof. Empirical data derived from this technique can be employed for process modeling, simulation and control of a sheetmaking system for making products comprising non-woven materials. A method of developing a mathematical model is to stimulate or perturb the sheetmaking process and measuring the responses, i.e., changes, if any, that result. The mathematical models can be used to regulate the system in order to control the crepe pitch and/or crepe fold orientation distribution of the sheet. Process control techniques for papermaking machines are further described, for instance, in U.S. Pat. Nos. 6,805,899 to MacHattie et al., 6,466,839 to Heaven et al., 6,149,770, to Hu et al., 6,092,003 to Hagart-Alexander et al, 6,080,278 to Heaven et al., 6,059,931 to Hu et al., 6,853,543 to Hu et al., and 5,892,679 to He, which are all incorporated herein by reference.

Figure 10:
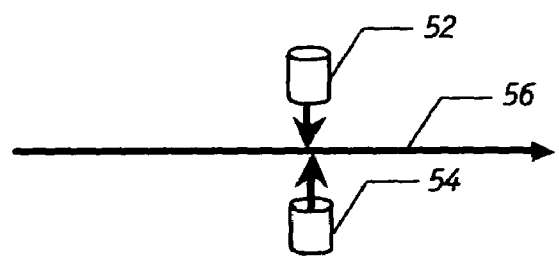
FIG. 10 illustrates deployment of the inventive crepe pattern measurement apparatus whereby both sides of the crepe sheet are monitored.

FIG. 10 illustrates an embodiment where both the reflective and transmissive modes of operation can be used to measure the crepe pattern on both sides of a web 56 which is preferably positionally constrained to travel in a relatively straight line without much fluttering, for instance, by tension or aerodynamics. In this case, both the upper and lower sides of the web are illuminated and/or imaged by device 52 and 54, respectively. Where the web can be transported unsupported, as at the dry end of a papermaking machine, both sides of the web can be measured simultaneously. If the unsupported web is opaque or nearly opaque, then the two sides of the web can be measured independently with two separate apparatuses 52 and 54 each operating in the reflective mode.

On the other hand, if the unsupported web is transparent or only partly opaque, measurement of both sides can be accomplished by employing two separate apparatuses 52 and 54 each operating in the reflective mode. Alternatively, the measurement of both sides can be accomplished by employing two separate apparatuses 52 and 54 each operating in the transmissive mode or the measurement of both sides can be accomplished by employing two separate apparatuses 52 and 54 one operating in the reflective mode and the other in the transmissive mode. Finally, the measurement of both sides can be accomplished by employing two separate apparatuses 52 and 54 one operating in the reflective mode and the other in the transmissive mode with the proviso that illumination is directed from only on side of the web.

The arrangement of FIG. 10 can be used, for example, to measure the crepe patterns on sheets that comprise multiple plies that are spliced together after formation to form a multiply product. The invention allows independent measurement and control of the crepe pattern in the plies that form the upper and lower surfaces of the multiply product.

The crepe pattern of a moving web can be monitored both in the cross direction and the machine direction. In the latter scenario, multiple crepe measurement apparatus can be positioned in tandem in the MD between the creping apparatus and the reel to optimize the process after creping. A continuous crepe pattern profile of the tissue after the Yankee can be generated compared to an "ideal" profile for making a particular grade of tissue. Depending on the degree of deviation from ideal, creping or conveying parameters (e.g. affecting tension or aerodynamics) can be adjusted accordingly. See, for example, U.S. Pat. No. 6,092,003 to Hagart-Alexander which is incorporated herein.

Similarly, for CD measurements, an array of apparatuses can be positioned along the CD at any suitable position of the papermaking machine. Alternatively, a scanning system that includes a single apparatus that is scanned across the width of a web can be employed. Scanner systems generally include pairs of horizontally extending guide tracks that span the width of the paper product to be monitored. The sensor is secured to a carriage that moves back-and-forth over to paper product as measurements are made. On-line scanning sensor systems for papermaking manufacture are disclosed in U.S. Pat. Nos. 4,879,471 to Dahlquist, 5,094,535 to Dahlquist et al., and 5,166,748 to Dahlquist, all of which are incorporated herein by reference.

The configuration as illustrated in FIG. 10, which employs both reflective and transmissive modes of operation, is particularly suited for measuring the top side and bottom side crepe pattern both in the CD and MD of paper. Crepe pattern profiles can be produced simultaneously. These measurements are directly or indirectly linked to other sheet properties like bulk and/or softness and/or absorbency. By making calibration crepe pattern measurements using paper having known sheet properties, a library can be established to correlate crepe pattern measurements and online measurements to actual bulk, softness, absorbency, and other characteristics.

Another aspect of the present invention relates to measuring the crepe fold orientation on the surface of the moving sheet. By "crepe fold" is meant, for instance, the crepe furrows on the hood side of tissue or equivalently of the crepe seams on the cylinder side of tissue. The crepe fold orientation measurements can be expressed as one or more different parameters that are used in controlling the papermaking process and/or characterizing the properties of the product. The parameters include, for instance: average crepe fold orientation angle, crepe fold orientation anisotropy index, and statistical distribution of crepe fold orientation angles.

The crepe fold orientation analysis method employs fractional-order gradients that are evaluated on at least two preferably orthogonal axes at a plurality of loci in the digital images obtained of a sheet being monitored. The evaluation loci preferably essentially cover an image of at least 10 mm in sheet width. Preferably, the fractional-order gradients are averaged or smoothed over small scales. A characteristic angle is formed from the at least two fractional gradients at each evaluation locus, for instance, by taking the arctangent of their ratio. The distribution of angles can then be characterized in various ways, such as by evaluating an average angle, or by fitting the distribution of angles to a specified parametric form.

If the digital image has blurring of features in the direction of movement of the sheet, a preprocessing procedure is preferably executed before the image is analyzed. For instance, a compensating blurring operation can be carried out in the orthogonal direction, but a deblurring or sharpening could be carried out in the direction of blur in some cases. If the sheet is non-opaque and there is a pattern in the background or if the sheet is transported on a forming fabric or other textured background, then the estimation of angles can be modified. This is important if the background texture is directional, such as for the forming fabrics in the fourdrinier section of a paper machine. For instance, the angles corresponding to those dominant in the background can be omitted from analysis when estimating the average angle or parameters of a distribution. Preferably, the background can be measured without the sheet, so that its characteristics can be determined.

While the crepe fold orientation analysis will be illustrated in measuring crepe fold orientation of paper, it is understood that the technique can be employed to determine orientations of crepe folds or wrinkles or other surface topography containing linear or nearly-linear features in a variety of products that are formed from non-woven fibrous materials including, for example, paperboard, tissue and the like. In addition, the orientation analysis has applicability outside products that are derived from cellulose.

The image-based measurement technique of the present invention estimates crepe fold orientation by analyzing digital images using gradient-type operators in two preferably orthogonal directions. The following summarizes some salient results from a field of mathematics, namely the fractional calculus, which unifies differentiation and integration as a single operation termed differintegration, and encompasses non-integer orders of differentiation and integration. The theory and methods of the fractional calculus are described, for example, in K. Oldham and J. Spannier, "The Fractional Calculus", Academic Press 1974, which is incorporated herein by reference.

Analytically, differintegration can be expressed concisely in integral transform function spaces. For example, let the Laplace transform of a function f(x) be denoted F(s), where s is the Laplace space parameter denoting the transformation of the variable x, and let the symbol $\mathcal{L}$ denote taking the transformation. Thus:

$$\mathcal{L}\{f(x)\} = F(s) = \int_{-\infty}^{+\infty} e^{-sx} f(x)\,dx. \tag{1}$$

Differintegration of a function to order q with respect to x corresponds to multiplication of its transform by the transform parameter s raised to the q-th power:

$$\mathcal{L}\left\{\frac{d^q}{d(x-a)^q}f(x)\right\} = s^q F(s). \quad (2)$$

Thus, as is apparent differintegration to a fractional order cannot be adequately represented as a combination of conventional differentiations or integrations to integer orders, and is a distinct operation. For example the semiderivative cannot be construed as a linear combination of the function and its derivative, any more than $s^{1/2}$ can be approximated as a combination of 1 and s.

While useful in symbolic mathematical analysis, the Laplace transform and other integral transform operators are unwieldy in practical numerical analysis of measured data. However, several formulations of generalized differintegration are mathematically equivalent and may be employed to construct a variety of algorithms for numerical differintegration. For instance, the Grünwald formulation defines the generalized differintegral of order q of a differintegrable function f(x) as:

$$\frac{d^q}{d(x-a)^q}f(x) = \lim_{N\to\infty}\left\{\frac{\left(\frac{x-a}{N}\right)^{-q}}{\Gamma(-q)}\sum_{k=0}^{N-1}\frac{\Gamma(k-q)}{\Gamma(k+1)}f\left(x-k\left(\frac{x-a}{N}\right)\right)\right\} \quad (3)$$

which in the limit relies on all values of the function in the interval from a to x. With q=1, and with a arbitrarily close to x, this yields the conventional derivative. With q=-1, it yields the conventional antiderivative (often termed the "indefinite integral") or the conventional integral (often termed the "definite integral"), depending on the choice of values for a and x.

The definition (Eq. 3) is valid and forms a numerically convergent series for all differintegrable functions of real, complex, or quaternion numbers (including discontinuous functions, provided they are finite). It also converges for arbitrary values of q, including complex and quaternion values of q. Other formulations of differintegration include those of Riemann, Liouville, Weyl, Heaviside, and Civin, among others. Some of these formulations are confined to specific situations, such as applying only to periodic functions. The Grünwald formulation is the most general and the Riemann-Liouville formulation is the next most general (it converges only when the real part of q is negative and requires analytic continuation with repeated conventional differentiation when the real part of q is positive, restricting it in these cases to continuous functions).

A number of numerical algorithms for performing differentiation to non-integer order are available; they present algorithms based on the Riemann-Liouville formulation as well as on the Grünwald formulation. A preferred algorithm is the Grünwald formulation as it directly yields convolutions of finite length for differintegration when the real part of the order is strictly positive. Of course other formulations can be used instead, if desired.

By omitting the limit in (3) and truncating the series to a finite number of terms N+1, with a fixed interval h between abscissae at which the function f(·) is known, an approximation for the differintegral of order q is obtained. For convenience and without loss of generality, we can set a=x−Nh, yielding:

$$\left(\frac{d^q}{dx^q}\right)_{-}f(x) = \frac{h^{-q}}{\Gamma(-q)}\sum_{k=0}^{N}\frac{\Gamma(k-q)}{\Gamma(k+1)}f(x-kh) \quad (4)$$

The weight factors applied to the function on the right hand side of (4) can be used as the convolution kernel in a convolution representation of differintegration, or as elements of a row in a matrix representation of differintegration. Note that although the gamma function $\Gamma(k-q)$ is unbounded when k−q is a negative integer, the ratio $\Gamma(k-q)/\Gamma(-q)$ is always finite, and can be computed using Stirling numbers of the first kind. The negative subscript on the operator on the left hand side of (Eq. 4) denotes that the expression on the right hand side is a backward-difference approximation to the differintegral at x, since it does not employ any function values at abscissae greater than x. However, a forward difference approximation can also be constructed from Eq. 3 with equal validity by reversing the sense of the interval [a,x], so that a=x+Nh before simplifying:

$$\left(\frac{d^q}{dx^q}\right)_{+}f(x) = -\frac{h^{-q}}{\Gamma(-q)}\sum_{k=0}^{N}\frac{\Gamma(k-q)}{\Gamma(k+1)}f(x-kh) \quad (5)$$

The positive subscript on the operator on the left hand side of (Eq. 5) denotes that the expression on the right hand side is a forward-difference approximation to the differintegral at x, since it does not employ any function values at abscissae less than x. The negation on the right-hand-side corrects for the change in direction of the differintegration. A centered difference approximation can be obtained by combining the forward difference and backward difference expressions. Thus, the convolution weights $w_k$ for a centered difference approximation to a differintegral of order q with 2N+1 terms are generated as:

$$w_k = \begin{cases} \dfrac{-h^{-q}\Gamma(-k-q)}{2\Gamma(-q)\Gamma(1-k)} & k < 0 \\ 0 & k = 0 \\ \dfrac{h^{-q}\Gamma(k-q)}{2\Gamma(-q)\Gamma(k+1)} & k > 0 \end{cases} \quad (6)$$

For example, with h=1, convolution kernels of 9 terms derived from (Eq. 6) using N=4 giving centered approximations to some differintegrals of fractional order not exceeding unity are (neglecting a factor of ½ for clarity):

| Order q | $w_{-4}$ | $w_{-3}$ | $w_{-2}$ | $w_{-1}$ |
|---|---|---|---|---|
| ¼ | −77/2048 | −7/128 | −3/32 | −¼ |
| ⅓ | −10/243 | −5/81 | −1/9 | −⅓ |
| ½ | −5/128 | −1/16 | −1/8 | −½ |
| ⅔ | −7/243 | −4/81 | −1/9 | −⅔ |
| ¾ | −45/2048 | −5/128 | −3/32 | −¾ |
| 1 | 0 | 0 | 0 | −1 |

| Order q | $w_0$ | $w_1$ | $w_2$ | $w_3$ | $w_4$ |
|---|---|---|---|---|---|

-continued

| | | | | | |
|---|---|---|---|---|---|
| 1/4 | 0 | 1/4 | 3/32 | 7/128 | 77/2048 |
| 1/3 | 0 | 1/3 | 1/9 | 5/81 | 10/243 |
| 1/2 | 0 | 1/2 | 1/8 | 1/16 | 5/128 |
| 2/3 | 0 | 2/3 | 1/9 | 4/81 | 7/243 |
| 3/4 | 0 | 3/4 | 3/32 | 5/128 | 45/2048 |
| 1 | 0 | 1 | 0 | 0 | 0 |

It can be seen that successive terms at either end of the kernel are declining in magnitude and that they decline less rapidly for orders closer to zero than for orders closer to unity (this observation cannot be generalized to orders of zero or less, or greater than unity). Also, the first term on either side of the center is equal in magnitude to the order of the differintegral, and thus is greater for orders close to unity than for orders close to zero, so that the significance of subsequent terms declines quite rapidly for orders above ½. For most purposes, a five term approximation is sufficiently accurate for orders greater than ½, while at least nine terms might be needed for orders below ¼.

In the above, the simplest algorithm has been used for developing numerical approximations to the differintegral. Other more sophisticated algorithms can be constructed, giving superior convergence properties, or requiring fewer numerical operations, or yielding a higher-order approximation. For example, Oldham and Spannier also give an algorithm in which a Lagrange interpolation is embedded, giving faster convergence. Similarly, various analytic techniques can be used to increase the accuracy of a finite series approximation beyond that obtained by merely truncating the infinite series expressions.

Let us now turn to application of differintegral operators to a digital image. Let S denote a set of plural locations in the image, which are preferably distributed symmetrically around the optical axis, or distributed randomly within a region which is symmetric around the optical axis. Let $D_x$ be a gradient-type operator in the x direction, and $D_y$ be a corresponding operator in the y direction. The gradient operators are preferably of non-integer order with order between ¼ and ¾. It is advantageous if the gradient-type operators are of the centered type. The gradient-type operators are applied to the image, for instance by convolution:

$$G_x = D_x \otimes I$$

$$G_x = D_x \otimes I \quad (7)$$

where the convolutions are evaluated at each pixel specified in S, producing local gradient estimates in each direction $G_x$ and $G_y$. It is advantageous to combine an averaging operation with the gradient-type operation, such that the gradient value computed for a particular pixel is a weighted average of values computed at plural pixels. It is particularly advantageous if such averaging is performed only in the direction orthogonal to the direction of the gradient-type operator, such that the averaging used in applying operator $D_x$ uses only pixels offset from each other in the y direction, and the averaging used in applying operator $D_y$ uses only pixels offset from each other in the x direction.

Note that considerable computational efficiency can be achieved by implementing the convolution of Eq. 7 using integer arithmetic instead of floating point arithmetic. This is trivial when the convolution kernel terms are differintegral approximations generated from the Grünwald formulation, since Eq. 6 intrinsically yields rational numbers as kernel coefficients if the interval h is unity (when expressed in suitable units), when the differintegral order is itself a rational number. A simple integer scaling then gives whole integer kernel values. Alternatively, an integer-valued kernel can be achieved without changing the units of h by including the factor $h^{-q}$ in the scaling. Similar considerations apply to non-convolution implementations of the gradient-type operation. Integer operations are generally much faster than floating point operations, so that images can be processed more quickly, or can be processed using less sophisticated computational apparatus.

These gradient values in the two directions contain the orientation information of structures at corresponding scales in the image. While the directions used for the gradient-type operators need not be orthogonal and need not coincide with the axes of the image, it is advantageous if they are orthogonal and also advantageous if they coincide with the axes of the image, since that maximizes the information content and simplifies subsequent processing, if any. The order of the gradient-type operator can be an integer, such as one (making it a conventional gradient), but it has been found that the results are more reliable when the order of the gradient-type operator is less than unity, and especially when it is between ¼ and ¾.

Summary information describing the crepe fold orientation can be extracted from the gradient values in numerous ways. An exemplary method is described here. An orientation angle is assigned to each analyzed pixel as:

$$\theta = \arctan\left(\frac{G_y}{G_x}\right) \quad (8)$$

and an orientation intensity for the pixel is assigned as:

$$J = \sqrt{(G_x)^2 + (G_y)^2} \quad (9)$$

A histogram is then formed, in which a nominal range of angles such as −90° to +90° is divided into plural finite intervals, preferably of equal width, and the orientation intensities are summed for all pixels whose assigned orientation angles are in the same interval, producing a histogram H(θ). This histogram represents the frequency distribution of orientation angles for the analyzed pixels of the image. This frequency distribution provides a valuable statistical representation of the crepe fold orientation of the paper. It is a common graphic representation of orientation distributions, often presented as a polar plot of amplitude versus angle.

The analysis can proceed further by reducing the frequency distribution to a small number of parameters, by fitting it to a standard statistical distribution of suitable form. For instance, the histogram can be fitted to a polar parametric form $$H(\theta) = \sqrt{A^2 \cos^2(\theta - \alpha) + B^2 \sin^2(\theta - \alpha)} \quad (10)$$

using least-squares or other methods. An estimate of the average or characteristic crepe fold orientation is given by the fitted parameter α if A>B, and by α±90° otherwise. The average crepe fold orientation angle is basically the angle of tilt of the ellipse relative to the machine direction. Similarly, if A>B, an estimate of the anisotropy of the crepe fold orientation distribution is given by:

$$e = \sqrt{\frac{A^2 - B^2}{A^2}} \quad (11)$$

in which A and B must be exchanged if B>A. An equivalent formulation of (10) which contains e as a parameter is:

$$H(\theta) = C(1 + e\cos(2\theta - 2\alpha)) \quad (12)$$

If the anisotropy is zero, then there is no characteristic orientation direction. High values of e indicate very strongly oriented sheets with a clearly dominant crepe fold orientation direction.

The crepe fold orientation anisotropy index is defined in Eq. 11. A is the length of the major axis and B is the length of the minor axis. If the sample is isotropic the distribution is a circle, A=B, and e=0. If all the folds are perfectly aligned, A is large, B~0 and e=1. Finally, statistical crepe fold orientation is the probability that a fold is oriented at a particular angle.

Note that Eq. 10 is by no means the only form suitable for fitting crepe fold orientation distributions in paper, but is probably the most common.

While the preferred order of the gradient-type operator is less than unity, the present invention is not confined to such orders, and encompasses use of differintegral operators of arbitrary order in the gradient-type evaluations, including pure integer orders.

The crepe fold orientation analysis also contemplates use of complex and quaternion order differintegral operators whose order has one or more nonzero imaginary parts. In this case, one or more additional steps can optionally be used to facilitate evaluation of the pixel angle such as in (Eq. 8) and pixel amplitude such as in (Eq. 9). The additional step is to form a suitable norm of a complex or quaternion number, for instance by forming the 2-norm of the value, or by taking its real part, or by forming a norm in a suitable inner-product space, and so forth. As is apparent, norms can be evaluated on a gradient value used in expressions used to compute pixel angle and amplitude such as (Eq. 8) or (Eq. 9), or can be evaluated on the angle and amplitude computed from non-normed values.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A computer implemented method for measuring crepe pattern features on a surface of a moving sheet that comprises the steps of:
   (a) illuminating an area on at least one side of the sheet with radiation and forming an optical image of the illuminated area using at least one lens with the proviso that no stabilizer to constrain the moving sheet to a narrow path is required;
   (b) obtaining and recording at least one digital image of the optical image of the illuminated area by employing an image detector wherein the digital image comprises a plurality of pixels and a pixel in the digital image represents a dimension in the moving sheet that does not exceed one quarter the nominal crepe pitch of the moving sheet so that the crepe pattern features can be discerned; and
   (c) calculating the crepe pattern features of the sheet by processing at least one digital image by evaluating at least one spectrum on a linear section through the digital image wherein the at least one spectrum represents physical spacing of the crepe pattern features that are discerned from the digital image wherein the crepe pattern features are characterized as at least one of: (i) an average folding pitch, (ii) a distribution of folding pitches, (iii) an average folding length, (iv) a distribution of folding lengths, and (v) a distribution of folding angles.

2. The method of claim 1 wherein at least one spectrum is evaluated using a Fourier transform.

3. The method of claim 1 wherein at least one spectrum is evaluated using a wavelet transform.

4. The method of claim 1 wherein at least one spectrum is evaluated using a Wigner-Ville transform.

5. The method at claim 1 wherein the crepe pattern is characterized as an average folding pitch.

6. The method of claim 1 wherein the crepe pattern is characterized as a distribution of folding pitches.

7. The method of claim 1 wherein the crepe pattern is characterized as an average folding length.

8. The method of claim 1 wherein the crepe pattern is characterized as a distribution of folding lengths.

9. The method of claim 1 wherein the crepe pattern is characterized as a distribution of folding angles.

10. The method of claim 1 wherein at least one digital image of the sheet is acquired on an illuminated side of the sheet.

11. The method of claim 1 wherein only one side of the sheet is illuminated and the at least one digital image of the sheet is acquired on the opposite side of the sheet where the sheet is illuminated.

12. The method of claim 1 wherein the crepe pattern features are measured for both surfaces of the moving sheet.

13. The method of claim 12 wherein at least one digital image is obtained from each side of the sheet.

14. The method of claim 1 wherein the radiation eon ins radiation with wavelengths in at least two separate wavelength regions and in step (b) at least two digital images of the illuminated area are acquired substantially simultaneously with the proviso that not all of the images obtained are derived from radiation having the same wavelength and step (c) calculates the crepe pattern features of rho sheet by processing the at two digital images.

15. The method of claim 1 wherein an step (a) comprises illuminating the area on the sheet with illumination that is directionally symmetric around an optical axis of the image detector.

16. The method of claim 15 wherein the illumination is provided by a plurality of light sources that are arranged in at least one annulus that is substantially concentric around the optical axis of the image detector.

17. The method of claim 1 further comprising the step of supporting the moving sheet with a support structure that is located on one side of the sheet and step (a) comprises illuminating an area on the other side of the sheet.

18. The method of claim 1 wherein the moving sheet is non-opaque with respect to the radiation and step (c) includes compensating for radiation that is transmitted through the sheet and which contains background images.

19. The method of claim 1 wherein the sheet is a multi-ply sheet comprising a plurality of plies of sheet material that are spliced together wherein the method is further characterized in that the crepe pattern, features of each of the plurality of plies of sheet material is measured as each ply is formed as a moving sheet.

20. The method of claim 1 wherein the moving sheet comprises a sheet tissue.

21. The method of claim 1 wherein the moving sheet comprises a sheet of tissue and the illuminated area on the sheet of tissue is located downstream from a Yankee cylinder.

22. The method of claim 21 further comprising comparing the crepe pattern features that are calculated in step (c) to a target crepe pattern features and, at least one of (i) changing the doctor blade of the Yankee cylinder (ii) adjusting doctor blade angle, or (iii) adjustment of application of additives to the Yankee cylinder surface.

23. The method of claim 1 wherein step (b) comprises obtaining a plurality of digital images of illuminated areas along a cross direction of the moving sheet.

24. A computer implemented method for measuring crepe pattern features on a surface of a moving sheet that comprises the steps of:
  (a) illuminating an area on at least one side of the sheet with radiation and forming an optical image of the illuminated area using at least one lens with the proviso that no stabilizer to constrain the moving sheet to a narrow path is required;
  (b) obtaining and recording at least one digital image of the optical image of the illuminated area by employing an image detector wherein the digital image comprises a plurality of pixels and a pixel in the digital image represents a dimension in the moving sheet that does not exceed one quarter the nominal crepe pitch of the moving sheet so that the crepe pattern features can be discerned; and
  (c) calculating crepe folding of the sheet by processing at least one digital image with a gradient operator that produces a gradient magnitude and direction for at least one of the pixels.

25. The method of claim 24 wherein step (c) employs a gradient operator of a non-integer order.

26. The method of claim 25 wherein the gradient operator has a non-integer order between $1/4$ and $3/4$.

27. A system for measuring crepe pattern features on a surface of a moving sheet that comprises:
  means for forming an optical image of an illuminated area on the surface of the moving sheet that includes at least one lens with the proviso that no stabilizer to constrain the moving sheet to a narrow path is required;
  image obtaining means, that includes an image detector, for obtaining and recording at least one digital image of the optical image of the illuminated area on the moving sheet wherein the digital image comprises a plurality of pixels and a pixel in the digital image represents a dimension in the moving sheet that does not exceed one quarter the nominal crepe pitch of the moving sheet so that the crepe pattern features can be discerned; and
  control means for calculating the crepe pattern features of the sheet by processing the at least one digital image wherein the control means evaluates at least one spectrum on a linear section through the digital image wherein the at least one spectrum represents physical spacing of the crepe pattern features that are discerned from the digital image wherein the crepe pattern features are characterized as at least one of: (i) an average folding pitch, (ii) a distribution of folding pitches, (iii) an average folding length, (iv) a distribution of folding lengths, and (v) a distribution of folding angles.

28. The system of claim 27 wherein the spectrum is evaluated using a Fourier transform or using a wavelet transform or using a Wigner-Ville transform.

29. The system of claim 27 wherein the image obtaining mean comprises a light source that directs radiation to illuminate an area on one side of the sheet and an imaging device that is positioned to obtain at least one digital image of the sheet on the illuminated side of the sheet.

30. The system of claim 27 wherein the image obtaining means includes a light source that directs radiation to illuminate only one side of the sheet and an imaging device that is positioned to acquire at least one digital image of the sheet from the opposite side of the sheet where the sheet is illuminated.

31. The system of claim 27 wherein the image obtaining means includes (i) a light source that provides radiation that contains radiation with wavelengths in at least two separate wavelength regions and (ii) in step (b) image detecting means for acquiring at least two digital images of the illuminated area substantially simultaneously with the proviso that not all the images obtained are derived from radiation having the same wavelength and the control means processes the at two digital images.

32. The system of claim 27 wherein the image obtaining means includes a light source that provides radiation that illuminates the area on the sheet with illumination that is directionally symmetric around an optical axis of the image detector.

33. The system of claim 32 wherein the illumination is provided by a plurality of light sources that are arranged in at least one annulus that is substantially concentric around the optical axis of the image detector.

34. The system of claim 27 further comprising control means for calculating the crepe fold orientation of the shed by processing the at least one digital image with a gradient operator.

35. The system of claim 34 wherein the gradient operator is of a non-integer order.

36. The system of claim 35 wherein the gradient operator has non-integer order of between $1/4$ and $3/4$.

37. The system of claim 34 wherein the gradient operator produces a gradient magnitude and direction for at least one of the pixels.

* * * * *

UNITED STATES PATENT AND TRADEMARK OFFICE
CERTIFICATE OF CORRECTION

PATENT NO. : 7,545,971 B2 Page 1 of 1
APPLICATION NO. : 11/209586
DATED : June 9, 2009
INVENTOR(S) : John F. Shakespeare It is certified that error appears in the above-identified patent and that said Letters Patent is hereby corrected as shown below:

In Column 22, line 46, delete "con ins" add --contains--;
In Column 22, line 52, delete "rho" add --the--;
In Column 22, line 54, delete "an";
In Column 24, line 47, delete "shed" add --sheet--.

Signed and Sealed this

Eighteenth Day of August, 2009

David J. Kappos
*Director of the United States Patent and Trademark Office*